United States Patent [19]

Dale

[11] 4,113,575
[45] Sep. 12, 1978

[54] SEPARATION OF ACETONE FROM N-BUTANE BY DISTILLATION

[75] Inventor: Glenn H. Dale, Bartlesville, Okla.

[73] Assignee: Phillips Petroleum Company, Bartlesville, Okla.

[21] Appl. No.: 669,539

[22] Filed: Mar. 23, 1976

[51] Int. Cl.$^2$ .............. B01D 3/40; C07C 49/08; C07C 9/10
[52] U.S. Cl. .................... 203/62; 203/73; 203/91; 260/593 P; 260/676 R
[58] Field of Search .......... 203/62, 91, 73, 78, 203/80; 260/677 A, 676 R, 593 P

[56] References Cited

U.S. PATENT DOCUMENTS

| | | | |
|---|---|---|---|
| 2,360,859 | 10/1944 | Evans | 208/240 |
| 2,371,908 | 3/1945 | Morris et al. | 55/85 |
| 2,377,049 | 5/1945 | Sauters | 203/78 |
| 2,449,610 | 9/1948 | Long | 203/62 |
| 2,461,993 | 2/1949 | McKinnis | 203/62 |
| 2,901,406 | 8/1959 | Kirshenbaum et al. | 203/75 |
| 2,911,452 | 11/1959 | Broughton | 260/677 A |
| 3,329,586 | 7/1967 | Pettingill | 203/78 |
| 3,527,837 | 9/1970 | Woerner et al. | 203/62 |
| 3,681,202 | 8/1972 | Funkhouser | 203/62 |
| 3,687,820 | 8/1972 | Akell | 203/80 |
| 3,798,132 | 3/1974 | Sarno | 203/62 |

OTHER PUBLICATIONS

Horsley; *Azeotropic Data,* 1952, pp. 318–328.
Robinson et al.; *The Elements of Fractional Distillation,* (1939), pp. 43 & 44.

*Primary Examiner*—Wilbur L. Bascomb, Jr.

[57] ABSTRACT

Fluid mixture of acetone and at least one hydrocarbon containing four-carbon atoms is separated by fractional distillation at a pressure low enough to eliminate formation of an azeotrope and a corresponding temperature.

6 Claims, No Drawings

SEPARATION OF ACETONE FROM N-BUTANE BY DISTILLATION

BACKGROUND OF THE INVENTION

This invention relates to a separation process. In particular, it relates to fractional distillation of a mixture containing acetone and at least one four-carbon atom hydrocarbon.

Mixtures of acetone and hydrocarbons containing four-carbon atoms are difficult to separate by conventional fractional distillation because of close boiling points of the component and/or because of the formation of azeotropes. Yet, such separation must be achieved as one of the steps in some commercial applications. For example, in the process of making butadiene from n-butane one of the intermediate steps — first dehydrogenation — results in creation of a mixture of n-butane and butylenes. Only butylenes are introduced into the second dehydrogenation zone; consequently, n-butane must be separated from butylenes. When the separation is carried out by extractive distillation with acetone, alone or in admixture with other solvents such as sulfolane, some of the acetone forms a mixture with n-butane, which must be separated if the ingredients are to be recycled. Failure to separate n-butane and acetone results in loss of acetone, which because the butane stream is relatively large represents an intolerable economic loss even at small concentrations of acetone.

One solution offered by the prior art is to contact the mixture with water. Acetone is selectively dissolved in water and then separated therefrom by distillation. The distillation of water-acetone mixture requires considerable amount of energy, thus making this approach economically and environmentally undesirable.

Another known approach is to employ an extractive solvent for separation of n-butane and acetone.

The present invention provides a novel method for separation of a mixture containing acetone and at least one hydrocarbon containing four-carbon atoms.

One object of the invention is to provide a method for separating acetone from hydrocarbons containing four-carbon atoms.

Another object of the invention is to provide a method for separating acetone from hydrocarbons containing four-carbon atoms without introduction of any other compounds, thus eliminating the possibility of contamination of separated products by additives.

Still another object of the invention is to provide a method for separating acetone from four-carbon hydrocarbons using conventional equipment for fractional distillation.

A further object of the invention is to prevent formation of azeotropes during fractional distillation of the mixture.

Still another object of the invention is to separate trace amounts of acetone from at least one four-carbon hydrocarbon.

A still further object of the invention is to simplify and improve the process of separating hydrocarbons containing four-carbon atoms from each other or one another using extractive distillation with acetone, by providing an improved way to separate acetone from the hydrocarbons after the extractive distillation step is completed.

SUMMARY OF THE INVENTION

In accordance with one aspect of the invention, acetone is separated from a mixture with at least one hydrocarbon containing four-carbon atoms by fractional distillation at a pressure low enough to prevent formation of azeotropes.

In accordance with another aspect of the invention, the formation of an azeotrope between acetone and at least one of the hydrocarbons containing four-carbon atoms is prevented by selecting a fractional distillation pressure below the one conventionally used.

In accordance with still another aspect of the invention, acetone is separated from a narrow boiling hydrocarbon or hydrocarbons containing four-carbon atoms by fractional distillation at a reduced pressure.

In accordance with a further aspect of the invention, after hydrocarbons containing four-carbon atoms are separated from each other or one another by extractive distillation with acetone, the acetone is then separated from individual hydrocarbons by distillation at a pressure low enough to prevent formation of azeotropes.

Still further aspects of the invention will become apparent upon studying this specification and the appended claims.

DETAILED DESCRIPTION OF THE INVENTION

Acetone is difficult to separate from hydrocarbons containing four-carbon atoms, such as, n-butane or butene-1 by conventional fractional distillation, i.e., distillation at a temperature of the top plate of 120° F (49° C) to permit condensation of the overhead product by cooling water and corresponding pressure of about 69 psia (0.476 MPa). The difficulty arises as a result of either narrow boiling points of the components or as a result of acetone forming an azeotrope with the hydrocarbon. It has been discovered that acetone can be separated by selecting an appropriate reduced pressure for fractional distillation. When the correct reduced pressure is chosen, formation of an azeotrope — such as n-butane-acetone azeotrope — is prevented permitting a substantially complete separation of the components. Similarly, by reducing the pressure, it is possible to separate constituents of narrow boiling range hydrocarbons.

The pressure to be chosen varies depending on the system, i.e., which of the four-carbon hydrocarbons is present with acetone. For n-butane-acetone azeotrope, the pressure of the distillation column required for elimination of the azeotrope and substantially complete separation of the components is below about 60 psia (0.414 MPa) and corresponding temperature of about 109° F (43° C). The preferred pressure ranges from about 45 psia (0.310 MPa) to about 20 psia (0.138 MPa), at which points corresponding fractionation temperatures are 92° F (33° C) and 40° F (4° C), respectively. Although the separation can be achieved at even lower pressures, that option is unattractive below 15 psia (0.103 Mpa), and corresponding temperature of 32° F (0° C), because vacuum becomes necessary and because the freezing point of cooling water is attained.

For a butylene-acetone system, which does not form an azeotrope, fractional distillation at a pressure below 60 psia (0.414 MPa) becomes more efficient, i.e., a better separation of the components can be achieved.

Of course, in those commercial applications which do not require a totally pure product, the preferred range is dictated by the economics of the operation at different conditions rather than by the degree of separation and the preferred mode of operation may be different from the one indicated. For example, in the process of making butadiene from n-butane, referred to in an earlier part of this application, when separation of n-butane and acetone is accomplished by the method of the invention, n-butane being more volatile of the two is taken off as a pure overhead product. Acetone, which is recycled to achieve the separation of n-butane and butylenes, need not be pure; consequently, the separation of the bottom product need not be complete. This practice of the invention allows considerable economic savings. The operating conditions for separation of n-butane and acetone can be chosen for a particular application from data presented in Example I.

In operation, the feed is introduced to a fractionating column which is kept at pressure at which azeotrope is not formed between acetone and the four-carbon hydrocarbon at or which separation of narrow boiling components can be achieved. The four-carbon hydrocarbon constitutes most of the overhead product which is partially condensed. The reflux is returned to the top of the column; the distillate is withdrawn. The bottom products contain substantially all acetone.

The invention can be further explained by reference to examples of operation.

The following examples illustrate the practicability of the invention but are not intended to place any limit upon the scope of the invention:

EXAMPLE I

| $X_1$, mole fraction of n-butane | T° F | T° C | P,psia | P, MPa (Megapascals) | Relative Volatility* |
|---|---|---|---|---|---|
| .98 | 90 | 32 | 43.4 | 0.299 | 1.200 |
| .985 | 90 | 32 | 43.4 | | 1.168 |
| .99 | 90 | 32 | 43.4 | | 1.137 |
| .995 | 90 | 32 | 43.4 | | 1.107 |
| .98 | 120 | 49 | 69.4 | 0.478 | 1.084 |
| .985 | 120 | 49 | 69.4 | | 1.059 |
| .99 | 120 | 49 | 69.4 | | 1.033 |
| .995 | 120 | 49 | 69.4 | | 1.008 |
| Azeotrope at 0.996 mole fraction of n-butane at 69.4 psia | | | | | |
| .98 | 130 | 54 | 80.2 | 0.553 | 1.050 |
| .985 | 130 | 54 | 80.2 | | 1.026 |
| .99 | 130 | 54 | 80.2 | | 1.003 |
| Azeotrope at 0.993 mole fraction of n-butane at 80.2 psia | | | | | |
| .995 | 130 | 54 | 80.2 | | 0.980 |
| .97 | 140 | 60 | 92.2 | 0.635 | 1.064 |
| .98 | 140 | 60 | 92.2 | | 1.018 |
| Azeotrope at 0.984 mole fraction of n-butane at 92.2 psia | | | | | |
| .985 | 140 | 60 | 92.2 | | 0.996 |

*Azeotrope is characterized by having relative volatility of 1.000.

This tabulation is the smoothed experimental data obtained in an equilibrium cell equipped for direct sampling of the liquid and vapor phases. The equilibrium cell contained n-butane-acetone mixture. The example demonstrates that azeotropes of n-butane-acetone can be broken by reducing fractionation pressure, allowing practically complete separation.

EXAMPLE II

The feed comprising 10.00 mole percent acetone and 90.00 mole percent of n-butane is introduced onto a feed tray near the middle of a nearly isothermal fractionating column with most temperature rise near the bottom of the column. The kettle temperature is 198° F (92° C); the temperature of the top tray is 90° F (28° C); and pressure of the column is 44 psia (0.303 MPa). The column has 40 theoretical trays. The overhead of the column is totally condensed. The reflux containing 99.9 mole percent of n-butane is returned to the top of the column; the distillate recovered contains 99.9 mole percent of n-butane. The bottom product contains 99.0 mole percent acetone. This example comprises calculations based upon experimental data.

EXAMPLE III

The feed comprising 10.00 mole percent acetone and 90.00 mole percent of n-butane is introduced onto a feed tray near the middle of a nearly isothermal fractionating column with most temperature rise near the bottom of the column. The kettle temperature is 150° F (66° C); the temperature of the top tray is 140° F (60° C); and pressure of the column is 100 psia (0.689 MPa). The column has 40 theoretical trays. The overhead of the column is totally condensed. The reflux containing 98.4 mole percent of n-butane is returned to the column; the distillate recovered from the totally condensed overhead contains 98.4 mole percent of n-butane. The bottom product contains 85.6 mole percent acetone. This example comprises calculations based upon experimental data.

I claim:

1. A process for separating a mixture consisting essentially of acetone and n-butane which mixture forms an azeotrope under conventional distillation conditions which comprises:
   (a) introducing the mixture into a fractionation zone and therein subjecting said mixture to fractional distillation conditions including pressures up to about 60 psia (0.414 MPa) and a corresponding temperature so that an azeotrope is not formed but the mixture is separated into an overhead containing substantially n-butane and a bottoms containing mainly acetone; and
   (b) withdrawing an overhead stream containing essentially n-butane and being essentially free of acetone and a bottoms stream containing essentially acetone.

2. A process of claim 1 wherein the corresponding temperature ranges from about 32° F (0° C) to about 109° F (43° C) respectively.

3. A process of claim 1 wherein the fractionation pressure is from about 20 psia (0.138 MPa) to about 45 psia (0.310 MPa) and the corresponding fractionation temperatures are from about 40° F (4° C) to about 93° F (33° C).

4. In a process for separating a mixture of n-butane from butylene including the steps of distilling the mixture in an extractive fractionation zone in the presence of acetone as a selective solvent and removing a stream consisting essentially of acetone and n-butane which mixture forms an azeotrope under conventional distillation conditions the improvement which comprises:
   introducing said stream into a second fractionation zone and therein subjecting it to such distillation conditions including pressures up to about 60 psia (0.414 MPa) and a corresponding temperature to cause separation of said stream into an overhead comprising mainly n-butane and a bottoms comprising mainly acetone; and
   withdrawing said overhead as an overhead stream and said bottoms as a bottoms stream.

5. A process as claimed in claim 4 wherein the the corresponding temperature is in the range from about 32° F (0° C) to about 109° F (43° C) respectively.

6. A process as claimed in claim 4 wherein the pressure in step (d) is in the range from about 20 psia (0.138 MPa) to about 45 psia (0.310 MPa) and the corresponding temperature ranges from about 40° F (4° C) to about 92° F (33° C) respectively.

* * * * *